(12) United States Patent
Gallaher

(10) Patent No.: US 6,713,069 B1
(45) Date of Patent: Mar. 30, 2004

(54) COMPOSITIONS AND METHODS FOR DETECTING, PREVENTING, AND TREATING AFRICAN HEMORRHAGIC FEVER

(75) Inventor: William R. Gallaher, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 08/838,128

(22) Filed: Apr. 15, 1997

Related U.S. Application Data
(60) Provisional application No. 60/058,210, filed on Apr. 16, 1996.

(51) Int. Cl.[7] .............................................. A61K 39/193
(52) U.S. Cl. ..................................... 424/218.1; 530/324
(58) Field of Search ........................... 424/186.1, 218.1; 530/300, 324

(56) References Cited

U.S. PATENT DOCUMENTS 4,880,779 A   11/1989   Gallaher ...................... 514/15

OTHER PUBLICATIONS

Volchkov, V.E., et al., 1995, "Gp mRNa of Ebola virus is edited by the Ebola virus polymerase and by T7 and vaccinia virus polymerases", Virol. 214:421–430.*
Sanchez, A., et al., 1993, "Sequence analysis of the Ebola virus genome: organization, genetic elements, and comparison with the genome of Marburg virus", Vir. Res. 29(3):215–240.*

Sanchez, A., et al., 1996, "The virion glycoproteins of Ebola viruses are encoded in two reading frames and are expressed through transcriptional editing.", Proc. Natl. Acad. Sci. USA 93(8):3602–3607.*

Blacklow, S., "A Trimeric Subdomain of the Simian Immunodeficiency Virus Envelope Glycoprotein," *Biochemistry*, vol. 34, pp. 14955–14962 (1995).

Cao, J., "Changes in the Cytopathic Effects of Human Immunodeficiency Virus Type 1 Associated with a Single Amino Acid Alteration in the Ectodomain of the gp41 Transmembrane Glycoprotein," *J. Virology*, vol. 68, pp. 4662–4668 (1994).

Cao, J. et al., "Effects of Amino Acid Changes in the Extracellular Domain of the Human Immunodeficiency Virus Type I gp41 Envelope Glycoprotein," *J. Virology*, vol. 67, pp. 2747–2755 (1993).

(List continued on next page.)

*Primary Examiner*—Laurie Scheiner
*Assistant Examiner*—Jeffrey S. Parkin
(74) *Attorney, Agent, or Firm*—John H. Runnels

(57) ABSTRACT

There is a substantial degree of structural similarity (although not sequence similarity) between the carboxy-terminal one-third of Filovirus glycoprotein and the transmembrane proteins of the very distantly related retroviruses, especially those of avian sarcoma viruses. The high degree of structural similarity implies functional homology as well. A number of compounds that are useful in the diagnosis and treatment of African hemorrhagic fever ("AHF") are disclosed. AHF infections (e.g., Ebola, Marburg) may be inhibited with low concentrations of peptides or antibodies of low toxicity. For example, analogs of a portion of the natural fusion glycoprotein of a Filovirus may be used to inhibit the normal fusion process of the virus in vivo, thus preventing or limiting infection.

2 Claims, 1 Drawing Sheet

OTHER PUBLICATIONS

Chambers, P., "Heptad Repeat Sequences are Located Adjacent to Hydrophobic Regions in Several Types of Virus Fusion Glycoproteins," *J. Gen. Virology*, vol. 71, pp. 3075–3080 (1990).

Delwart, E. et al., "Retroviral Envelope Glycoproteins Contain a 'Leucine Zipper'–like Repeat," *AIDS Res. Human Retroviruses*, vol. 6, pp. 703–706 (1990).

Gallaher, W., "Detection of a Fusion Peptide Sequence in the Transmembrane Protein of Human Immunodeficiency Virus," *Cell*, vol. 50, pp. 327–328 (1987).

Gallaher, W. et al., "A General Model for the Surface Glycoproteins of HIV and other Retroviruses," AIDS Res. Human Retroviruses, vol. 11, pp. 191–202 (1995).

Gallaher, W. et al., "A General Model for the Transmembrane Proteins of HIV and other Retroviruses," AIDS Res. Human Retroviruses, vol. 5, pp. 431–440 (1989).

Gallaher, W. et al., "Membrane Interactions of Human Immunodeficiency Virus," pp. 113–142 in R. Aloia et al. (eds.), Membrane Interactions of HIV (1992).

Jiang, S. et al., "HIV–1 Inhibition by a Peptide," Nature, vol. 365, p. 113 (1993).

Lambert, D., "Peptides from Conserved Regions of Paramyxovirus fusion (F) Proteins are Potent Inhibitors of Viral Fusion," *Proc. Natl. Acad. Sci. USA*, vol. 93, pp. 2186–2191 (1996).

Owens, R. et al., "Oligopeptide Inhibitors of HIV–Induced Syncytium Formation," AIDS Res. Human Retroviruses, vol. 6, pp. 1289–1296 (1990).

Richardson, C. et al., "Specific Inhibition of Paramyxovirus and Myxovirus Replication by Oligopeptides with Amino Acid Sequences similar to Those at the N–Termini of the F1 or HA2 Viral Polypeptides," Virology vol. 105, pp. 205–222 (1980).

Sanchez, A. et al., "Sequence Analysis of the Ebola Virus Genome: Organization, Genetic Elements, and Comparison with the Genome of Marburg Virus," *Virus Research*, vol. 29, pp. 215–240 (1993).

Schwartz, D. et al., "Nucleotide Sequence of Rous Sarcoma Virus," Cell, vol. 32, pp. 853–869 (1983).

Volchkov, V. et al., "The Envelope Glycoprotein of Ebola Virus contains an Immunosuppressive–like Domain Similar to Oncogenic Retroviruses," *FEBS Lett.*, vol. 305, pp. 181–184 (1992).

Wild, C. et al., "A Synthetic Peptide Inhibitor of Human Immunodeficiency Virus Replication: Correlation Between Solution Structure and Viral Inhibition," Proc. Natl. Acad. Sci. USA, vol. 89, pp. 10537–10541 (1992).

Wild, C. et al., "A Synthetic Peptide from HIV–1 gp41 is a Potent Inhibitor of Virus–Mediated Cell–Cell Fusion," *AIDS Res. Human Retroviruses*, vol. 9, pp. 1051–1053 (1993).

Wild, C. et al., "Peptides Corresponding to a Predictive α–Helical Domain of Human Immunodeficiency Virus Type 1 gp41 Are Potent Inhibitors of Virus Infection," *Proc. Natl. Acad. Sci. USA*, vol. 91, pp. 9770–9774 (1994).

Wild, C. et al., "The Inhibitory Activity of an HIV Type 1 Peptide Correlates with Its Ability to Interact with a Leucine Zipper Structure," *AIDS Res. Human Retroviruses*, vol. 11, pp. 323–325 (1995).

Will, C. et al., "Marburg Virus Gene 4 Encodes the Virion Membrane Protein, a Type 1 Transmembrane Glycoprotein," *J. Virol.*, vol. 67, pp. 1203–1210 (1993).

Wilson, I.A., "Structure of the Haemagglutinin Membrane Glycoprotein of Influenza Virus at 3Å Resolution," *Nature*, vol. 289, pp. 366–373 (1981).

Sanchez, A., et al., 1993, "Sequence analysis of the Ebola virus genome: organization, genetic elements, and comparison with the genome of Marburg virus.", Vir. Res. 29(3):215–240.*

Volchkov, V. E., et al., 1992, "The envelope glycoprotein of Ebola virus contains an immunosuppresive–like domain similar to oncongenic retroviruses", FEBS Letters 305(3):181–184.*

* cited by examiner

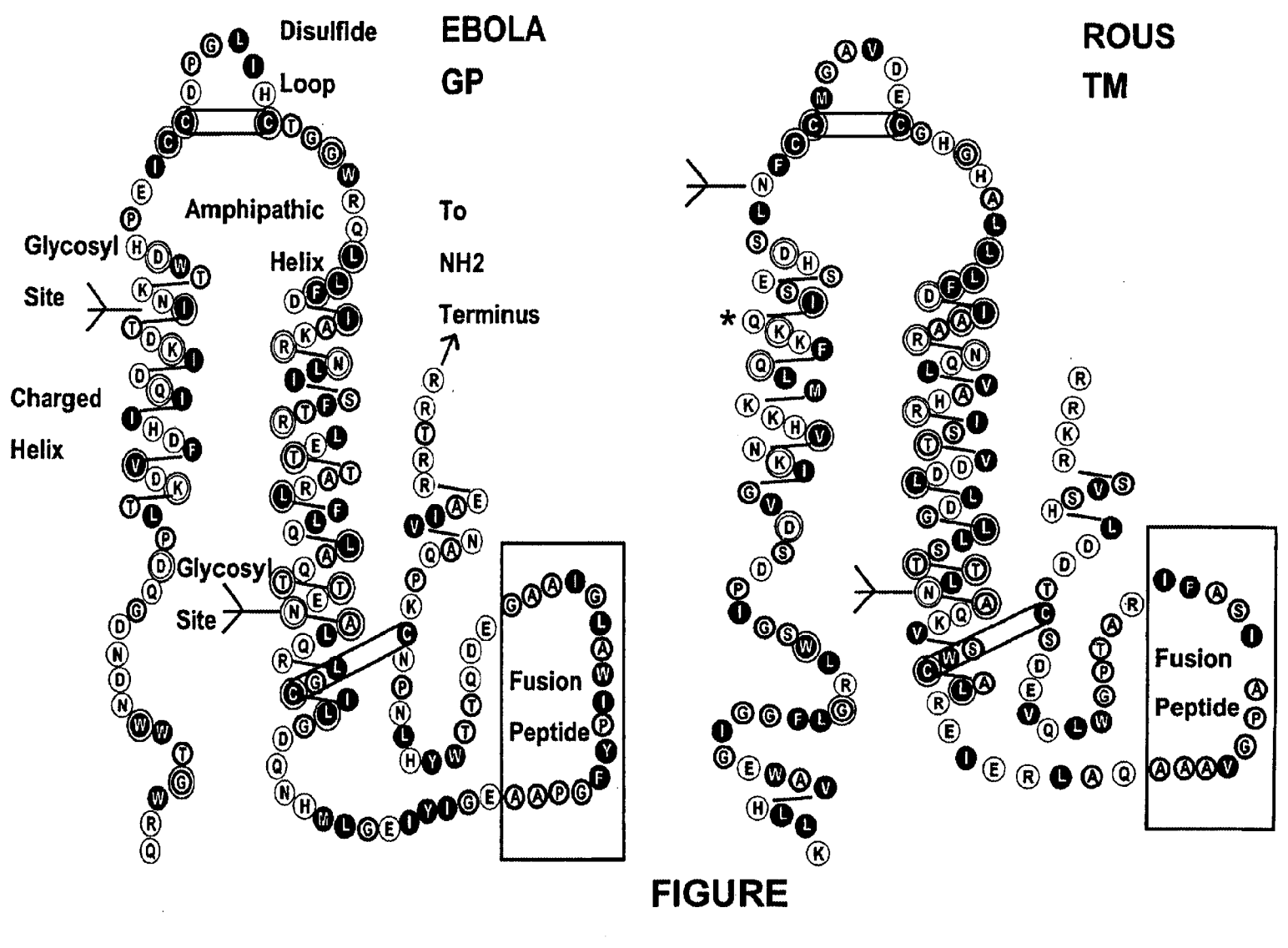

FIGURE

COMPOSITIONS AND METHODS FOR DETECTING, PREVENTING, AND TREATING AFRICAN HEMORRHAGIC FEVER

The benefit of the Apr. 16, 1996 filing date of provisional application No. 60/058,210 is claimed under 35 U.S.C. §119(e).

This invention pertains to compositions and methods for detecting, preventing, and treating African Hemorrhagic Fever (AHF). More specifically, the invention pertains to detecting, preventing, and treating infection by the viral agent that causes African Hemorrhagic Fever with the use of antigenic or inhibitory peptides.

Viruses

Many different viruses cause disease in humans and other animals. Viral infections are responsible for many epidemics, including influenza, herpes, and AIDS. Efforts to prevent or cure viral diseases have been hampered by the unusual structures and functions of viruses, which are quite unlike those of other infectious agents such as bacteria, fungi, and protozoa.

A virus consists essentially of a nucleic acid genome surrounded by a lipid-protein envelope. A virus multiplies by invading a host cell and causing the cell to synthesize and package viral components under the control of the viral nucleic acid. Viruses frequently mimic normal cellular mechanisms, making it difficult to synthesize drugs that are selectively toxic to viruses.

The viral envelope, formed from proteins and glycoproteins, is critical to the successful entry of a virus into a host cell. A common pattern exists in the attachment or adsorption of viral particles onto host cell membranes for several "families" of viruses, including the filoviruses, paramyxoviruses, influenza viruses, and retroviruses. An "attachment" or "receptor-binding" viral glycoprotein binds to a specific receptor on the host cell surface. Following attachment of the virus, fusion of the target cell membrane with the viral envelope is promoted by a viral fusion glycoprotein, which probably penetrates the host cell at a particular site and then contracts, drawing the two entities closer together. Following fusion, the contents of the virus merge with the cytoplasm of the cell, and the viral nucleic acid then redirects the cell machinery to effect its own multiplication.

The viral invasion mechanism can potentially be disrupted at any of several points to prevent the virus from gaining access to the inside of a cell. One such means is to block the receptor sites of the viral fusion glycoprotein, or otherwise to prevent the viral fusion glycoprotein or its receptor site from carrying out the attachment or fusion. Such blocking has been achieved for paramyxoviruses with oligopeptides mimicking the binding function of a paramyxovirus viral fusion peptide. See C. Richardson et al., "Specific Inhibition of Paramyxovirus and Myxovirus Replication by Oligopeptides with Amino Acid Sequences similar to Those at the N-Termini of the $F_1$ or $HA_2$ Viral Polypeptides," *Virology* vol. 105, pp. 205–222 (1980).

Peptides containing the sequence Phe-X-Gly (or analogs) are known to inhibit HIV-1. See U.S. Pat. No. 4,880,779; and W. Gallaher et al., "Membrane Interactions of Human Immunodeficiency Virus," pp. 113–142 in R. Aloia et al. (eds.), *Membrane Interactions of HIV* (1992); the latter of which also discusses the structure of the HIV-1 gp41 TM protein.

C. Wild et al., "A Synthetic Peptide Inhibitor of Human Immunodeficiency Virus Replication: Correlation Between Solution Structure and Viral Inhibition," *Proc. Natl. Acad. Sci. USA*, vol. 89, pp. 10537–10541 (1992); and C. Wild et al., "A Synthetic Peptide from HIV-1 gp41 is a Potent Inhibitor of Virus-Mediated Cell-Cell Fusion," *AIDS Res. Human Retroviruses*, vol. 9, pp. 1051–1053 (1993) described peptide analogues of the HIV-1 fusion peptide that also inhibit HIV-1. These peptide analogs interfere with the normal function of the fusion protein, thereby preventing fusion and subsequent infection of the cell by the virus. See also C. Wild et al., "The Inhibitory Activity of an HIV Type 1 Peptide Correlates with Its Ability to Interact with a Leucine Zipper Structure," *AIDS Res. Human Retroviruses*, vol. 11, pp. 323–325 (1995); and C. Wild et al., "Peptides Corresponding to a Predictive α-Helical Domain of Human Immunodeficiency Virus Type 1 gp41 Are Potent Inhibitors of Virus Infection," *Proc. Natl. Acad. Sci. USA*, vol. 91, pp. 9770–9774 (1994).

S. Jiang et al., "HIV-1 Inhibition by a Peptide," *Nature*, vol. 365, p. 113 (1993), reported inhibition of HIV-1 with a peptide corresponding to a different portion of the gp41 glycoprotein.

R. Owens et al., "Oligopeptide Inhibitors of HIV-Induced Syncytium Formation," *AIDS Res. Human Retroviruses*, vol. 6, pp. 1289–1296 (1990) describes the antiviral activity of an analog of the HIV fusion peptide.

While such results are promising, it is typically not possible to extrapolate treatment for one type of virus to other unrelated types: each family of viruses is typically characterized by unique glycoproteins, which may vary within families, or even among variants within a viral "genus." It is most uncommon to find structural homologues between unrelated or distantly related viral groups, such that an inhibitory compound for one group will also be effective for the other. The variability in envelope structure, type of nucleic acid genome, the arrangement of nucleic acid, and the mechanisms for replicating and packaging the genome are all factors making the treatment of viral disease unpredictable. This variability explains the fact that there are no broad spectrum antiviral agents that might be comparable to broad spectrum antibacterial agents. When considering possible therapeutic regimens, each group of viruses, and even viruses within the same virus family, must be considered separately.

I. A. Wilson, "Structure of the Haemagglutinin Membrane Glycoprotein of Influenza Virus at 3 Å Resolution," *Nature*, vol. 289, pp. 366–373 (1981) first described the x-ray structure of a viral transmembrane protein, namely that of influenza virus, including the relative positions of the fusion peptide and a helical core structure that organized the glycoprotein complex on the surface of the viral particle.

P. Chambers, "Heptad Repeat Sequences are Located Adjacent to Hydrophobic Regions in Several Types of Virus Fusion Glycoproteins," *J. Gen. Virology*, vol. 71, pp. 3075–3080 (1990) noted an amphipathic helical motif in the paramyxoviruses, such as measles virus.

E. Delwart et al., "Retroviral Envelope Glycoproteins Contain a 'Leucine Zipper'-like Repeat," *AIDS Res. Human Retroviruses*, vol. 6, pp. 703–706 (1990) discussed the structures of several retroviral glycoproteins.

J. Cao, "Changes in the Cytopathic Effects of Human Immunodeficiency Virus Type 1 Associated with a Single Amino Acid Alteration in the Ectodomain of the gp41 Transmembrane Glycoprotein," *J. Virology*, vol. 68, pp. 4662–4668 (1994), reported that site-directed mutagenesis of one amino acid in the gp41 transmembrane protein of HIV-1 substantially reduced cytopathicity of the virus by reducing fusion activity.

S. Blacklow, "A Trimeric Subdomain of the Simian Immunodeficiency Virus Envelope Glycoprotein," *Biochemistry*, vol. 34, pp. 14955–14962 (1995) confirmed the trimeric structure of the HIV glycoprotein complex, and the participation of antiparallel amphipathic helices in the formation of those trimers.

D. Lambert, "Peptides from Conserved Regions of Paramyxovirus fusion (F) Proteins are Potent Inhibitors of Viral Fusion," *Proc. Natl. Acad. Sci. USA*, vol. 93, pp. 2186–2191 (1996) disclosed peptide analogues of putative antiparallel amphipathic helices in paramyxovirus fusion proteins inhibited those viruses.

African Hemorrhagic Fever

African Hemorrhagic Fever ("AHF") is a viral disease of great concern to the human population. Relatively little is known about the agents that cause AHF. The AHF viruses belong to the Filovirus family, which to date are known to include only Ebola virus and Marburg virus. The Filoviridae family of viruses is characterized by the presence of a single-stranded RNA molecule and RNA transcriptase in the virion.

Human AHF infections have presumably resulted either directly from human contact with the natural reservoir of the agent in the wild, or indirectly from human contact with other primates who have acquired it from the natural reservoir. To date AHF outbreaks have been relatively rare, involving one to at most a few hundred humans, but in recent years the frequency of such outbreaks has increased. Primates, including humans, appear to be accidental, dead-end hosts for the virus, with further infections being limited to those in close contact with infected individuals. However mortality in humans is high, ranging from 25–90% (depending on the strain), typically 50–80%. Filoviruses are investigated only in Biosafety Level 4 facilities.

The natural reservoir of Filoviruses remains unknown, despite intensive searches by scientists from the Centers for Disease Control, the United States Army Medical Research Institute of Infectious Diseases, and the World Health Organization. Given the severity of the disease in humans, and the fact that the natural reservoir of the disease remains unknown, Filoviruses are regarded as extremely dangerous agents with enormous latent potential to cause human morbidity and mortality. "A hot virus from the rain forest lives within a twenty-four-hour plane flight from every city on earth." R. Preston, *The Hot Zone*, pp. 11–12 (1994).

To date, no attempts to control or cure the disease in infected individuals have been shown to be successful. In the most recent outbreak in Kikwit, Zaire, some patients infected during the later stages of the epidemic were treated with immune serum taken from convalescing patients who were infected during earlier stages of the epidemic. The patients treated with immune serum survived. The serum treatment possibly had beneficial effects, although the protocols used for these treatments and the lack of controls made scientific evaluation of the results nearly impossible—for example, it is possible that the virulence of the pathogen became attenuated during later stages of the epidemic, and that administration of the serum was superfluous. Other investigators reported that neutralizing antibodies could not be found in the serum of convalescing patients. Even if the administration of immune serum is found to be beneficial, any major outbreak of AHF would soon overwhelm the limited supply of immune serum.

Scientists from the Virological Center of Institute of Microbiology of the Russian Ministry of Defense recently immunized horses with dead Ebola Zaire virus, and then challenged the horses with live Ebola Zaire virus. The horses were then bled to produce an antiserum whose effectiveness is currently being evaluated as an Ebola treatment. Similar antiserum experiments are underway in other laboratories using goats, sheep, pigs, and monkeys.

Filoviruses appear to infect cells by the attachment-fusion process described above. Gene 4 of Ebola or Marburg codes for the viral envelope glycoprotein. The sequences of the envelope glycoproteins, determined from Ebola and Marburg virus isolates obtained in 1976 and 1982, respectively, have been described by A. Sanchez et at., "Sequence Analysis of the Ebola Virus Genome: Organization, Genetic Elements, and Comparison with the Genome of Marburg Virus," *Virus Research*, vol. 29, pp. 215–240 (1993); and C. Will et al., "Marburg Virus Gene 4 Encodes the Virion Membrane Protein, a Type I Transmembrane Glycoprotein," *J. Virol.*, vol. 67, pp. 1203–1210 (1993). The envelope glycoprotein is apparently unique, and shows no significant homology over an extended sequence with that of any other known protein. The glycoprotein contains 666–681 amino acids, and can be aligned among various viral isolates with a limited number of gaps. A limited level of sequence similarity with an immunosuppressive retroviral transmembrane protein sequence has been described, over a 26 amino acid region in the carboxy-terminal one-third of the protein that is relatively conserved among the Ebola and Marburg viruses. V. Volchkov et al., "The Envelope Glycoprotein of Ebola Virus contains an Immunosuppressive-like Domain Similar to Oncogenic Retroviruses," *FEBS Lett.*, vol. 305, pp. 181–184 (1992). Twelve of the twenty-six positions (46%) are identical in the Ebola virus and in avian sarcoma viruses. In the remaining carboxy-terminal one-third, of about 152 positions only 27 are identical (17.7%), even after introducing 7 gaps of 1–11 amino acids in either sequence. V. Volchkov et al. hypothesized that the conserved region might be explained by recombination between different viral RNA's. Other than raising the question of whether the identified 26 amino acid region might have an immunosuppressive role, the published work has attributed no structural or functional significance to any part of the AHF glycoprotein sequence outside the presumed membrane-spanning domain, a domain that is highly similar for many type I membrane glycoproteins.

Even though the primary amino acid sequence of the AHF glycoprotein has been known for several years, there has been no previous success in using that information to produce inhibitory compounds effective against filoviral infections.

Unexpected Structural Similarity to Retroviral Proteins

It has been unexpectedly discovered that there is a substantial degree of structural similarity (although not sequence similarity) between the carboxy-terminal one-third of Filovirus glycoprotein and the transmembrane proteins of the very distantly related retroviruses, especially those of avian sarcoma viruses. The high degree of structural similarity implies functional homology as well. The discovery of this functional homology has led to the unexpected discovery of a number of compounds that are useful in the diagnosis and treatment of AHF infections. AHF infections may be inhibited with low concentrations of peptides of low toxicity. For example, analogs of a portion of the natural fusion glycoprotein of a Filovirus may be used to inhibit the normal fusion process of the virus in vivo, thus preventing or limiting infection.

The discovery of structural homology with retroviral glycoproteins could not be accomplished by the use of standard protein analysis software, as the limited amino acid identities are insufficient. Rather, the discovery of homology only resulted from a detailed analysis of the secondary structure of the glycoprotein. The discovery of structural homology with only limited sequence homology implies that the ancestors of filoviruses and retroviruses diverged long ago.

Comparing the overall sequences of the glycoproteins of Marburg and Ebola viruses, it was found that of the 666–681 amino acids, the first 180–200 are relatively constant, the next 300–350 are quite variable, and the last 180 or so amino acids are relatively constant. This third (relatively constant) region is that which has been found to be homologous to the transmembrane protein of retroviruses.

Because the corresponding peptide regions of the retrovirus HIV-1 have been found to include sites of antibody recognition, as well as sequences that may be used as potent inhibitors of replication, discovery of the structural homology has led to the discovery of a number of reagents that are clinically useful in detecting and treating AHF.

Despite the fact that only minimal sequence similarity exists, a high degree of structural similarity was found between the carboxy-terminal one-third of Filovirus glycoprotein and the transmembrane proteins of avian sarcoma viruses. This structural similarity extended to regions having little or no sequence identity. This analysis revealed for the first time that the Filovirus and Retrovirus transmembrane regions are members of a superfamily of functional protein homologs that are found in a number of virus families, and that are responsible for effecting entry of viruses into host cells.

A structural alignment highlighted several sequence motifs homologous to motifs in HIV-1 that have previously been reported to play specific functional roles in HIV biology, or in the response to HIV infection. Several structural and functional regions of Filovirus GP have now been identified as being useful in the detection, prevention, and inhibition of AHF.

The structure of the Filovirus glycoprotein ("GP") was determined by methods generally similar to those used in W. Gallaher et al., "A General Model for the Transmembrane Proteins of HIV and other Retroviruses," *AIDS Res. Human Retroviruses*, vol. 5, pp. 431–440 (1989); and W. Gallaher et al., "A General Model for the Surface Glycoproteins of HIV and other Retroviruses," *AIDS Res. Human Retroviruses*, vol. 11, pp. 191–202 (1995). Briefly, probable structures were evaluated by different publicly available protein analysis software packages. Areas where the structures generated by the different programs were similar were found on inspection to have structures with at least partial similarity to those of Rous sarcoma virus ("RSV") transmembrane ("TM") protein. "Manual" comparison of the remaining regions of the glycoprotein revealed a strong likelihood that the structure of the entire carboxy-terminal one-third was homologous to that of the RSV TM protein.

The results of the structural analysis are depicted in the accompanying figure showing models for the carboxy-terminal 181 amino acids of Ebola GP, and Rous sarcoma virus TM. Note that the two structures appear to be nearly identical, despite the differences in sequence.

At 152–155 amino acids before membrane insertion, there is a polybasic region in both viruses that in RSV serves as the site for cleaving the precursor into the surface and TM glycoproteins of the amino-terminal sequence. Because no similar cleavage of Ebola GP has been reported, and because this polybasic site is displaced in the Marburg virus 62 amino acids toward the amino terminus, the functional significance of this similarity with the RSV TM glycoprotein is unknown.

Within 8–9 amino acids, in both Ebola GP and in Rous sarcoma virus TM there is a 37–46 amino acid region bounded by cysteines, a region that presumably forms a disulfide-defined loop structure. At the center of this region is a sequence of 14–16 uncharged and hydrophobic amino acids that appear in the same relative position as the homologous sequences in fusion peptides that have experimentally been found to be critical for viral entry and cell fusion in other retroviruses, including HIV. The Marburg virus contains within this region the canonical Paramyxovirus fusion tripeptide FFG, conservatively substituted with YFG in Ebola, and with FLG in HIV. See C. Richardson et al., "Specific Inhibition of Paramyxovirus and Myxovirus Replication by Oligopeptides with Amino Acid Sequences similar to Those at the N-Termini of the $F_1$ or $HA_2$ Viral Polypeptides," Virology vol. 105, pp. 205–222 (1980); and W. Gallaher, "Detection of a Fusion Peptide Sequence in the Transmembrane Protein of Human Immunodeficiency Virus," *Cell*, vol. 50, pp. 327–328 (1987). It has previously been shown that small peptides containing this tripeptide sequence or homologs are capable of inhibiting the fusion process of the AIDS virus, thus providing a useful form of therapy and prophylaxis for individuals exposed to retroviral infections, particularly HIV-1. See U.S. Pat. No. 4,880,779. Similarly, this tripeptide sequence and its homologs will inhibit the fusion process of filoviruses, thus providing a useful form of therapy and prophylaxis for individuals exposed to filoviral infections. Further, a high degree of identity between the Ebola and Marburg subfamilies occurs in this hydrophobic loop region. A. Sanchez et al., "Sequence Analysis of the Ebola Virus Genome: Organization, Genetic Elements, and Comparison with the Genome of Marburg Virus," *Virus Research*, vol. 29, pp. 215–240 (1993). The context of this fusion domain, defining a sharp turn equidistant between the cysteine (C) residues forming a disulfide loop, is reminiscent, within the Retrovirus family, of the context in which the fusion domain of avian sarcoma/leukosis virus is placed. The fusion motif itself, rich in proline (P) and glycine (G) residues, is similar to that of the Togaviruses, whose natural reservoir is in birds. The natural reservoir of Filoviruses has not yet been found. The avian-like character of the context and sequence of the fusion peptide region suggests that the natural reservoir of this virus family might be asymptomatic infection of birds, with only accidental infection of primates and man.

Next, beginning just prior to the second cysteine, and proceeding for 42 amino acids, there is in both Ebola virus and RSV a region with a high propensity to form an amphipathic helix similar to that found in every Retrovirus that has thus far been examined:

```
                                                               Ebola
NQDGLICGLRQLANETTQALQLFLRATTELRTFSILNRKAIDFLLQRWGGT
||  |  | || ||| |    |  | || ||| ||||  || ||||||  |||||
NQNNLVCRLRRLANQTAKSLELLLRVTTEERTFSLINRRAIDFLLTRWGGT
```

-continued (SEQ. ID NOS. 9 and 10, respectively)

Marburg

See W. Gallaher et al., "A General Model for the Transmembrane Proteins of HIV and other Retroviruses," *AIDS Res. Human Retroviruses*, vol. 5, pp. 431–440(1989). Homology of this region of Ebola GP with Retroviral TM proteins is reinforced by the finding that 17 of 42 amino acids are identical between Ebola and RSV throughout this region, including a site for N-linked glycosylation 7 amino acids after this second cysteine. Mutations in HIV-1 gp41 in the homologous region have inhibited infectivity and fusion potential in HIV. J. Cao et al., "Effects of Amino Acid Changes in the Extracellular Domain of the Human Immunodeficiency Virus Type I gp41 Envelope Glycoprotein," *J. Virology*, vol. 67, pp. 2747–2755 (1993).

Within 7–8 amino acids beyond this helical region are a pair of vicinal cysteines separated by 6 amino acids, a region that is homologous to the most conserved motif in the Retrovirus family of glycoproteins. In HIV-1 this region forms a disulfide loop structure that defines a highly conserved antigenic site. This loop region will also be antigenic in filoviruses.

Overlying the latter third of the amphipathic helix and the two vicinal cysteines is a peptide having immunosuppressive properties, a region that is 46% identical between Ebola and RSV. This potentially immunosuppressive region defines a center of identity between Ebola and Marburg subfamilies of 81%. See A. Sanchez et al., "Sequence Analysis of the Ebola Virus Genome: Organization, Genetic Elements, and Comparison with the Genome of Marburg Virus," *Virus Research*, vol. 29, pp. 215–240 (1993).

Within 2–9 residues beyond the vicinal cysteines is a second N-linked glycosylation site that is conserved throughout the Retrovirus family (even if not always utilized), and that is shared by Ebola and Marburg viruses. This glycosylation site lies either prior to or within a second region with a high charge density and a high potential to form an amphipathic helix. Of the 41 amino acids lying between the cysteines and the membrane insertion region of Ebola GP, there are 9 identical amino acids between Ebola and RSV; and 17 are identical between Ebola and Marburg viruses. The identical amino acids are centered in the region of highest helical potential, with 9 of 24 positions identical between Ebola and RSV, and 10 of 24 between Ebola and Marburg.

Beyond this region toward the carboxy-terminus, the remainder of the sequence diverges between Ebola and RSV, except for the membrane-spanning domain, a domain that is highly similar for many type I membrane glycoproteins. RSV contains 11 additional amino acids prior to the membrane insertion domain, and 25 additional amino acids in the cytoplasmic tail. Even within the Retrovirus family there is a great deal of variation in the size and sequence of these regions following the vicinal cysteines, prior to and following the membrane-spanning hydrophobic region, such that diversity between Ebola and RSV in this region does not detract from the overall similarity observed.

This unexpected identification of regions with structural similarities for the first time permits alignment of sequences where homology would otherwise not be apparent. Localization of the second highly-charged helical region of Ebola GP permits its alignment with a region of similar character within the much larger region between the vicinal cysteines and membrane insertion domain in HIV-1 gp41. Based on the prior identification of this similarly highly charged region of HIV-1, a peptide analogue named DP-178 has been found to inhibit HIV infection and fusion at very low dosages. See C. Wild et al., "A Synthetic Peptide from HIV-1 gp41 is a Potent Inhibitor of Virus-Mediated Cell-Cell Fusion," *AIDS Res. Human Retroviruses*, vol. 9, pp. 1051–1053 (1993); see also C. Wild et al., "A Synthetic Peptide Inhibitor of Human Immunodeficiency Virus Replication: Correlation Between Solution Structure and Viral Inhibition," *Proc. Natl. Acad. Sci. USA*, vol. 89, pp. 10537–10541 (1992); and W. Gallaher et al., "A General Model for the Transmembrane Proteins of HIV and other Retroviruses," *AIDS Res. Human Retroviruses*, vol. 5, pp. 431–440 (1989).

Table 1 shows the alignment of RSV, Ebola, and Marburg with the 36 amino acids of DP-178. Although identities are limited, 5 with RSV, 6 with Marburg, and only 3 with Ebola, the identification of structural similarity implies that a peptide analogue to either charged helical region of Ebola and Marburg will have significant antiviral activity.

TABLE 1

```
           YTSLIHSLIEESQNQQEKNEQELLELDKWASLWNWF              HIV-1 dp178
              |     |     | |       |
CEDIAGMCCFNLSDHSESIQKKF-QLMKEHVNKIGVDSDPIGSWLRGLFGG              Rous
 |   ||    |   | |    | | | |   | |    |
CHILGPDCCIEPHDWTKNITDKIDQIIHDFVDKTLPDQGDNDNWWTGWRQW             Ebola
 |  |||||||   |  |||  ||||  |        |   |||
CKVLGPDCCIGIEDLSKNISEQIDQIKKDEQKEGTGW-GLGGKWWTSDWGV           Marburg
              | |   | |  ||          |
           YTSLIHSLIEESQNQQEKNEQELLELDKWASLWNWF              HIV-1 dp178
     (SEQ. ID NOS. 11, 12, 13, 14, and 11,
respectively)
```

Novel Treatments and Diagnostics

The discovery of these structural homologies for the first time allows the design of peptides useful in the treatment and diagnosis of filovirus infections. Among these peptides are five preferred sequences from the carboxy-terminal portion of Filovirus glycoprotein, or their homologs. The five sequences follow:

First is the cleavage sequence, RRTRR (SEQ. ID NO. 1). Second is the fusion peptide sequence, GAAIGLAWIPYF-GPAAEGIY (SEQ. ID NO. 2). Third is the amphipathic helix essential for infection, DGLICGLRQLAN-ETTQALQLFLRATTELRTFSILNRKAIDFLLQRWG (SEQ. ID NO. 3). Fourth is the apical disulfide loop, CHILGPDCC (SEQ. ID NO. 4). Fifth is the charged helical region essential for infectivity, HDWTKNITDKIDQIIHD-FVDKTLPDQGDNDNWWTGWRG (SEQ. ID NO. 5).

Other sequences of amino acids that will be useful for these purposes include the following sequence from the amino-terminal region of the Ebola glycoprotein: CRYVH-KVSGTGPCAGDFAFHKEGAFFLYDRLASTVIYRGTTF (SEQ. ID NO. 6), and the following two similar sequences that are believed to represent a direct repeat of a motif within the central region of the Ebola glycoprotein (homology shown):

```
SPQSLTTKPGPDNSTHNTPVYKLDISEATQVEQ (SEQ. ID NO. 7)
   | ||  ||         ||    |
SDTPSATTAAGPPKA-ENTNTSKSTDFLDPATTT (SEQ. ID NO. 8)
```

Homologous sequences for Marburg are NFSTLSAP-LQTTNDNTQS (SEQ. ID NO. 47) and SKKGPATTAP-NTTNEHFTSPPTP (SEQ. ID NO. 48).

Each of SEQ. ID NO's 1–8 above are taken from Ebola virus, Zaire strain. These sequences are readily alignable with the corresponding sequences from Marburg virus and other Filovirus strains.

Included within the scope of the present invention are discrete changes to the natural sequences that may inactivate pathogenesis without abolishing infectivity, and that, if introduced into the virus itself by techniques known to those practiced in the art of molecular biology, would result in a vaccine strain of the virus or its glycoprotein. Specific examples known to produce such inactivation are small deletions or insertions just prior to or after a functional sequence, or replacement of a single rare amino acid, such as tryptophane, with another amino acid, such as replacing FLLQRWG (SEQ. ID NO. 15) with FLLQRMG (SEQ. ID NO. 16) in the amphipathic helix region; or the replacement of an amino acid having little or no side chain such as glycine or alanine with an amino acid having more bulk, such as changing FLLQRWG (SEQ. ID NO. 15) to FLLQRWV (SEQ. ID NO. 17); or a combination of such substitutions, for example changing FLLQRWG (SEQ. ID NO. 15) to FLLQRMV (SEQ. ID NO. 18).

Mindful that these sequences were derived from 1976 and 1982 isolates of these Filoviruses, and also that viruses undergo mutagenic changes in sequence with time, amino acid substitutions, deletions, and insertions may be made at any position shown to be subject to natural variation. Likewise, new variants of Filoviruses may be discovered that are alignable with these sequences by standard computer methods known to those practiced in the art of protein analysis. This invention is intended to include sequences that are structural or functional homologues of those specified herein, as trivial alterations in response to natural variation of the Filovirus family over the period normally covered by a Patent. Furthermore, persons of ordinary skill in the art will appreciate that, in general, amino acid substitutions of the following types may be made without substantially affecting the activity of a peptide: an acidic amino acid may be substituted for another acidic amino acid; a basic amino acid may be substituted for another basic amino acid; a hydrophobic amino acid may be substituted for another hydrophobic amino acid; and a hydrophilic amino acid may be substituted for another hydrophilic amino acid. Such variations in the sequence of the peptides are also considered to be within the scope of this invention.

Each of these peptides may be used, in whole or in part, to achieve optimal activity. Each may be bordered by additional amino acids, either from the natural viral sequence, or by other amino acids as may be found useful, for example, to stabilize their native conformation, to increase activity, or to improve the pharmacologic properties of the active region.

An "inhibitory amount" of a peptide is defined as an amount effective to elicit antiviral antibody or antiviral lymphocytes in an animal or human inoculated with the peptide, sufficient to substantially inhibit or neutralize Filovirus; or to directly inhibit the infectivity or cytopathogenicity of a Filovirus, so as to reduce or eliminate the pathological manifestations of Filovirus-induced disease.

Antibodies or lymphocytes elicited by inoculation can also be used by those practiced in the immunological arts to detect and type filoviruses.

As used throughout the specification and claims, the word "inhibit" with respect to the activity of the therapeutic peptides is to be understood as meaning inhibition both in a prophylactic sense, i.e., prevention of the initial transmission of the virus to an individual; as well as in the sense of preventing an infection from becoming established or ameliorating its effects once the virus has been introduced into the body. Reference to an "AHF virus" is intended to encompass any filovirus associated with fever, hemorrhage, or other signs and symptoms in humans as defined by the Centers for Disease Control. Throughout the specification and claims, the abbreviation "AHF" will be used to interchangeably indicate infection by any member of the Filoviridae family of viruses that is infectious to humans.

BRIEF DESCRIPTION OF THE DRAWING

The accompanying FIGURE depicts models of the structures of the carboxy-terminal transmembrane region of Ebola Virus glycoprotein (SEQ. ID NO. 49) and of the transmembrane protein of Rous Sarcoma Virus (SEQ. ID NO. 50). Helices are indicated in helical net projection, with sequential amino acids connected by solid lines. Disulfide linkages are indicated by double dotted lines. Hydrophobic amino acids are grouped with a solid background; neutral amino acids with a heavily outlined circle; hydrophilic amino acids with a light circle. Regions described in the specification are labeled on the FIGURE. Additional information given includes the site and number of additional amino acid positions needed to align the two sequences, indicated by an asterisk. Also, double circles indicate amino acids that are identical in the two sequences. The Ebola, Zaire sequence was taken from A. Sanchez et al., "Sequence Analysis of the Ebola Virus Genome: Organization, Genetic Elements, and Comparison with the Genome of Marburg Virus," *Virus Research*, vol. 29, pp. 215–240 (1993); residues 497–650, Genbank U31033. The Rous Sarcoma, Prague C virus sequence is taken from D. Schwartz et al., "Nucleotide Sequence of Rous Sarcoma Virus," Cell, vol. 32, pp. 853–869 (1983); residues 402–554, Genbank J02342.

PEPTIDES USEFUL IN TREATMENT AND DIAGNOSIS

For the first, polybasic site, the pentapeptide RRTRR (SEQ. ID NO. 1) has the minimum length for an active peptide. However, given the susceptibility of such a peptide to inactivation by tryptic proteases, if the peptide is administered orally or in serum, additional amino acids may be added to present a native configuration or to inhibit drug inactivation. The native sequence including this sequence in Ebola is AGVAGLITGGRRTRREAIVNAQPK (SEQ. ID NO. 19). These sequences act as an antigenic site, and accordingly may be used either as part of a vaccine, or as part of an antibody assay for the diagnosis or detection of AHF infection.

For the second, fusion peptide sequence, active analogs contain the core heptapeptide WIPFFGP (SEQ. ID NO. 20) or WIPYFGP (SEQ ID NO. 21), or their inverses PGFFPIW (SEQ. ID NO. 22) or PGFYPIW (SEQ. ID NO. 23), the minimum sequence lengths required for inhibition, but the addition of further amino acids at either the N- or C-terminus of these peptides will not affect the activity of the active portion of the peptide. Theoretically, there is no particular limit to the number of additional amino acids that could be added, but in practical terms the length of the therapeutic peptide sequence will be limited by commercial feasibility, as well as the increasing potential for allergenic or immunogenic reactions with longer peptides. Generally speaking, the preferred peptide will have no more than about 6–9 amino acids on either side in addition to the critical sequences WIPFFGP (SEQ. ID NO. 20), WIPYFGP (SEQ ID NO. 21), PGFFPIW (SEQ. ID NO. 22), or PGFYPIW (SEQ. ID NO. 23). More inclusive sequences in the naturally occurring fusion peptide are GAAIGLAWIPYFGPAAEGIY (SEQ. ID NO. 2) (Ebola); CNPNLHYWTTQDE-GAAIGLAWIPYFGPAAEGIYIEG LMHNQDGLIC(SEQ.ID NO.24)(Ebola); DLAA-GLSWIPFFGPGIEGLY (SEQ. ID NO. 25) (Marburg); and CDAELRIWSVQEDDLAAGLSWIPFFG-PGIEGLYTAVLIKNQNNLVC (SEQ. ID NO. 26) (Marburg). These peptides are believed to function by blocking access to a receptor on cell surfaces.

For the third, amphipathic helix, a core sequence for interacting with the filovirus helix is

DGLICGLRQLANETTQALQLFLRATTEL-
RTFSILNRKAIDFLLQRWG (SEQ. ID NO. 3).

Some specific sequences that will be used to interfere with the helix-helix interaction in Ebola include the following:

NQDGLICGLRQLANETTQALQLFLRAT-
TELRTFSILNRKAIDFLLQRWGGT (SEQ. ID NO. 9)

NQDGLICGLRQLANETTQALQLFLR (SEQ. ID NO. 28)

ATTELRTFSILNRKAIDFLLQRWGGT (SEQ. ID NO. 29)

LRQLANETTQALQLFLRATTELRTFSILNRK
AIDFLLQR (SEQ. ID NO. 30)

QALQLFLRATTELRTFSILNRK (SEQ. ID NO. 31)

These sequences are believed to function by competitively inhibiting interaction between the two helices of the glycoprotein, blocking an essential conformation of the molecule.

For the fourth, disulfide loop region, the minimum sequence is CHILGPDCC (SEQ. ID NO. 4) for Ebola or CKVLGPDCC (SEQ. ID. NO. 32) for Marburg. A preferred embodiment would include additional amino acids on either side to foster correct folding. An example from the natural sequence for Ebola would be

QRWGGTCHILGPDCCIEPHD (SEQ. ID NO. 33).

The homologous loop region is the most constant feature known in retroviral glycoproteins, and define an epitope in HIV that is recognized by antibodies in nearly all HIV-positive patients. These epitopes may thus be useful both in eliciting a protective immune response (either as a vaccine or as a treatment during infection), and as a means to detect infection through immunological assays known in the art, including for example precipitin reactions, enzyme-linked immunosorbent assays, agglutination reactions, radioimmunoassays, Western blotting, immunofluorescence, and competitive binding assays.

For the fifth, charged helical region, the extended sequence for Ebola is CHILGPDCCIEPHDWTKNITD-KIDQIIHDFVDKTLPDQGDNDNWWTGWRQW (SEQ. ID NO. 13); an intermediate sequence is HDWTKNITD-KIDQIIHDFVDKTLPDQGDNDNWWTGWRG (SEQ. ID NO. 5); and the active, central sequence is ITDKIDQHH-DFVDKTL (SEQ. ID NO. 35) for direct inhibition of Ebola virus infection. The minimum core sequence for eliciting or reacting to antiviral antibody capable of inhibiting Ebola virus infection is GDNDNWWT (SEQ. ID NO. 36).

The comparable sequences for Marburg are CKVLGPD-CCIGIEDLSKNISEQIDQIKKDEQKEGT-GWGLGGKWWTSDWGV (SEQ. ID NO. 14); EDLSK-NISEQIDQIKKDEQKEGTGWGLGGKWWTSDWGV (SEQ. ID NO. 38); and ISEQIDQIKKDEQKEGT (SEQ. ID NO. 39).

In addition to competitively inhibiting interaction between the two helices of the glycoprotein, this region following the vicinal cysteines is also a source of both antiviral peptide analogues and of antigenic components.

The three additional sequences in the amino-terminal and central regions of the prototype Ebola sequence, namely CRYVHKVSGTGPCAGDFAFHKEGAFFLY-DRLASTVIYRGTTF (SEQ. ID NO. 6), and

```
SPQSLTTKPGPDNSTHNTPVYKLDISEATQVEQ (SEQ. ID NO. 7)
    |  ||  ||         ||   |
SDTPSATTAAGPPKA-ENTNTSKSTDFLDPATTT (SEQ. ID NO. 8)
``` contain core sequences that may also be used to inhibit interaction of the Ebola virus glycoprotein with host cells. For the first of the above sequences the core sequence is HKEGAFFLYDR (SEQ. ID NO. 40). For the second and third of the above sequences the core sequence is the region containing the identities between the sequences indicated by the connecting lines, namely SLTTKPGPDNSTHNTPVYK (SEQ. ID NO. 41) and SATTAAGPPKAENTNTSK (SEQ. ID NO. 42), respectively. A preferred embodiment includes these core sequences bounded by flanking sequences, for example SEQ. ID NO's 7 and 8 above, to achieve proper configuration, as either direct inhibitors of Ebola infectivity, or as Ebola-specific antigens. Homologous sequences for Marburg are NFSTLSAPLQTTNDNTQS (SEQ. ID NO. 47) and SKKGPATTAPNTTNEHFTSPPTP (SEQ. ID NO. 48).

As one example, the following peptides will be synthesized, and will be tested for toxicity against a number of cell cultures of human and other primate cell lines. Once safety is shown, the antiviral properties of the peptides will be confirmed at a laboratory working with Ebola virus under stringent Biosafety Level 4 conditions.

HDWTKNITDKIDQIIHDFVDKTLPDQGDNDN (SEQ. ID NO. 43)

HDWTKNITDKIDQIIHDFVDKTL (SEQ. ID NO. 44)

DKIDQIIHDFVDKTL (SEQ. ID NO. 45)

DKIDQIIHDFVDKTLPDQGDNDN (SEQ. ID NO. 46)

The arrangement of the amino acids outside the active sequence is not critical. If there are amino acids both before and after the active sequences, for economic reasons it is preferred to have not more than 6–8 before the designated peptide, and not more than 6–8 after the designated peptide.

The peptide may also be double ended, i.e., with an active sequence appearing at both ends, with intervening amino acids. The peptide may also comprise a tandem repeat. The identity of the additional amino acids, if present, is not particularly critical to the activity of the compound, and may be any of the known amino acids. Generally speaking, the addition of further residues to the central peptide sequence may be used to increase the solubility of the peptide as a whole, and therefore in general hydrophilic amino acids are preferred. Also, unless context indicates otherwise, it is contemplated that the terms "amino acid" and "peptide" as used in the specification and the claims refer to compositions including both the naturally occurring amino acids, as well as synthetic forms with modified side chains to increase solubility, biological half-life, or uptake and delivery to body tissues. Among such commonly used modifications are the addition of an acetyl, amido, N-carbobenzoxy, or O-sulfatyl group. Such modifications may also be used to increase the solubility of the peptides, and therefore facilitate the preparation of therapeutically useful compositions. Both D- and L-forms of all amino acids are also contemplated. D-amino acids are particularly useful on the ends of the peptides, as they are not susceptible to exopeptidases, and can therefore extend the biological half-life of the peptides in vivo. D-amino acids may also particularly be useful in the amphipathic helices, whose properties are dominated by the overall conformation and charge distribution.

Eliciting an Immune Response

BalbC mice will be inoculated intraperitoneally with 10 to 100 micrograms of peptide in an adjuvant suspension. The mice will be boosted with a second intraperitoneal injection of 25% of the original dose 4 weeks later, followed by an intramuscular injection of 25% of the original dose two weeks after the first booster. At 8–12 weeks after inoculation, serum will be harvested from the mice by standard methods known in the immunological arts. Antibody derived from the serum will be tested for its ability to react with the eliciting peptide suspension. After further boosting of antibody-positive animals, if indicated, the animals will be sacrificed, their spleens harvested, and the splenocytes will be used to prepare hybridomas secreting monoclonal antibodies specific for the eliciting antigen according to standard methods known in the immunological arts.

Alternately, human peripheral blood may be processed to yield a suspension of lymphocytes. These lymphocytes may be stimulated in vitro by standard methods and exposed to the peptides in an appropriate cellular and cytokine environment to stimulate the cells to secrete antibodies in vitro, using standard methods in the immunological arts for "in vitro immunization." The resulting cell lines may then be used to prepare hybridomas secreting human monoclonal antipeptide antibodies by standard methods known in the immunological arts. The resulting human monoclonal antibodies may then be used as medical reagents in detection, prevention, or therapy of filoviral infection.

Antiviral Testing In Vitro

Either from 1 nm to 1000 nm of the peptides, or 0.2 ml of from 1/10 to 1/2000 dilutions of antipeptide immune serum, will be suspended in 5.0 ml Dulbecco's minimal essential medium (DMEM) containing 10% fetal bovine serum. Each dilution of drug or antibody will be inoculated into cultures of the E6 subclone of the African green monkey cell line designated "Vero." In Biosafety Level 4 facilities, the cultures will then be inoculated for 1 hour at 37° C. in triplicate with an infective dose of each of the following viral strains: Ebola Zaire; Ebola Sudan; Ebola Reston; and Marburg Popp. The cultures will be incubated at 37° C. in a 5% $CO_2$ environment for 72 hours. Every 6 hours the cultures will be scored for viral replication by observation of the cultures for apparent cytopathology on a 1 plus to 4 plus basis. A dose/response curve for inhibition will be determined by comparing the effects at each dosage of each treatment to the cytopathology occurring in the absence of any treatment. Once the effective concentration to inhibit 50% of cytopathology (EC50) is determined, that EC50 will be compared to the toxic dose to determine safety, if any of the peptides or other antiviral treatments being tested have previously demonstrated toxicity through standard toxicity tests. It is expected that EC50 will be well below the level at which any toxicity is observed.

Antiviral Testing In Vivo

Several monkey species and hamsters are used as animal models of Filoviral infection. These animals will be inoculated by various routes with either peptides or antibodies, each labeled radioactively to trace their tissue concentrations, to determine the biological and pharmacological properties of the reagents according to standard methods known to the pharmaceutical industry. Once safety and pharmacokinetics in vivo are established, the animals will be inoculated with a dosage of the peptide or antibody at levels to establish a minimal inhibitory concentration in the plasma over an extended period of time, namely a time that is consistent with a practical administration schedule in the field. Once a potentially antiviral state is achieved, the animals will be challenged in Biosafety Level 4 conditions with an infective dose of virus to demonstrate protection of the animals against viral infection.

Once safety and efficacy in animals are demonstrated, safety in humans will be established through standard procedures in the pharmaceutical arts. Demonstrating efficacy in humans is subject to ethical constraints. Some ways in which efficacy in humans might be tested in an ethical manner include the following: administering immunogenic peptides to workers in Biosafety Level 4 facilities who are subject to the possibility of accidental infection; administering immunogenic peptides to individuals in a region where an outbreak of AHF has occurred; administering immunogenic peptides to a population in an area prone to periodic outbreaks of ARF; administering antiviral peptides or antibodies to individuals who are infected with AHF during an outbreak; administering antiviral peptides or antibodies to individuals who have been exposed to the risk of filoviral infection, but who are not yet demonstrating symptoms, for example to apparently healthy individuals in an area suffering from an AHF outbreak, or to a laboratory worker in a Biosafety Level 4 facility who may be accidentally exposed to virus (e.g., through a tear or puncture in a safety suit).

Miscellaneous

The active peptides may be employed in the form of pharmaceutically acceptable salts, particularly salts with various inorganic or organic bases. Among the salts that may be prepared are ammonium alkali metal salts, alkaline earth metal salts, and salts with organic bases such as dicyclohexamine.

The active peptides of the present invention are easily prepared by any of several known methods, including solid state synthesis on a peptide synthesizer or expression by a genetically engineered cell such as *E. coli*. See, e.g., Jakubke et al., "Amino Acids, Peptides and Proteins," pp. 77–183, Wiley & Sons (1977). Among the more commonly used techniques are coupling via the dicyclohexylcarbodiimide method or the solid phase Merrifield synthesis, in which a protected amino acid is bound to a resin particle as an ester bond. Amino acids having functional side chains, such as tyrosine, are generally protected with an easily removed blocking group, examples of which are well known to the skilled artisan. Alternately, the indicated active sequence may be expressed as a fusion protein by inserting a fragment of nucleic acid capable of coding for the sequence into an expression vector and incorporation into a host such as *E. coli*, using techniques that are well known to those practiced in the art of molecular genetics. See, e.g., J. Sambrook et al. (eds.), *Molecular Cloning: A Laboratory Manual* (2nd ed. 1989). Such expressed fusion proteins, e.g. any of the above specified peptides linked to a carrier protein by a polyhistidine bridge, may then be purified, followed by cleavage and purification of the peptide from the carrier protein to which it was fused.

The active peptides or antibodies may be administered in a number of forms, which may vary depending upon the therapeutic intent. A particularly important use of the present invention is its use for prophylactic purposes. For this purpose, the compounds may be applied topically or transdermally, in the form of ointments and aqueous compositions, including solutions, suspensions, creams, lotions, aerosol sprays, or dusting powders. The compounds may also be prepared and used in suppository form. The methods of preparation of such formulations, and pharmaceutically acceptable carriers for such formulations, are well known in the pharmaceutical art. Application of the therapeutic preparations may be to any area of the body that is a potential site of transmission of the virus, e.g., epidermally on cut or broken skin, vaginally, rectally or orally.

Alternately, the compounds may be prepared for oral or parenteral administration. In oral administration capsules or tablets may be prepared in which the peptides are combined with stabilizers, excipients, carriers, preservatives or flavors, as is common in pharmaceutical practice. For parenteral administration, i.e., intravenous, intramuscular, subcutaneous, or intraperitoneal administration, the peptides or antibodies are administered with a pharmaceutically acceptable carrier such as a sterile solution containing other solutes, for example, sufficient saline or glucose to make the solution isotonic.

The appropriate dosage will depend upon the mode of administration, and may readily be determined by those of ordinary skill in the art. Modification of the dosage range may also depend on whether the compounds are used prophylactically or for inhibiting an established infection. Such modifications will be apparent to one skilled in the art. The use of the peptides for prophylaxis is particularly advantageous.

Although the treatment of greatest interest is, of course, AHF viruses in humans, the utility of the present method is not so limited. The filovirus group may be found to include other pathogens of both humans and animals. Therefore, the present method has both human and veterinary application.

The complete disclosures of all references cited in this specification are hereby incorporated by reference. In the event of an otherwise irreconcilable conflict, however, the present specification shall control.

I claim:

1. A peptide consisting of SEQ. ID No. 5; wherein said peptide optionally contains no more than six to nine additional amino acid residues on the amino terminus of said amino acid sequence; and wherein said peptide optionally contains no more than six to nine additional amino acid residues on the carboxy terminus of said amino acid sequence.

2. A peptide as recited in claim 1, wherein said peptide consists of SEQ. ID No. 5.

* * * * *

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (v) FRAGMENT TYPE: internal (vi) ORIGINAL SOURCE:
      (A) ORGANISM: Ebola Virus
      (B) STRAIN: Zaire-Mayinga (xi) SEQUENCE DESCRIPTION: SEQ ID NO:1:

Arg Arg Thr Arg Arg
1            5

(2) INFORMATION FOR SEQ ID NO:2:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (v) FRAGMENT TYPE: internal (vi) ORIGINAL SOURCE:
            (A) ORGANISM: Ebola Virus
            (B) STRAIN: Zaire-Mayinga (xi) SEQUENCE DESCRIPTION: SEQ ID NO:2:

Gly Ala Ala Ile Gly Leu Ala Trp Ile Pro Tyr Phe Gly Pro Ala Ala
1               5                   10                  15

Glu Gly Ile Tyr
            20

(2) INFORMATION FOR SEQ ID NO:3:

(i) SEQUENCE CHARACTERISTICS:
            (A) LENGTH: 47 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Ebola Virus
            (B) STRAIN: Zaire-Mayinga (xi) SEQUENCE DESCRIPTION: SEQ ID NO:3:

Asp Gly Leu Ile Cys Gly Leu Arg Gln Leu Ala Asn Glu Thr Thr Gln
1               5                   10                  15

Ala Leu Gln Leu Phe Leu Arg Ala Thr Thr Glu Leu Arg Thr Phe Ser
                20                  25                  30

Ile Leu Asn Arg Lys Ala Ile Asp Phe Leu Leu Gln Arg Trp Gly
            35                  40                  45

(2) INFORMATION FOR SEQ ID NO:4:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Ebola Virus
            (B) STRAIN: Zaire-Mayinga (xi) SEQUENCE DESCRIPTION: SEQ ID NO:4:

Cys His Ile Leu Gly Pro Asp Cys Cys
1               5

(2) INFORMATION FOR SEQ ID NO:5:

(i) SEQUENCE CHARACTERISTICS:
            (A) LENGTH: 38 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Ebola Virus (B) STRAIN: Zaire-Mayinga (xi) SEQUENCE DESCRIPTION: SEQ ID NO:5:

```
His Asp Trp Thr Lys Asn Ile Thr Asp Lys Ile Asp Gln Ile Ile His
1               5                   10                  15

Asp Phe Val Asp Lys Thr Leu Pro Asp Gln Gly Asp Asn Asp Asn Trp
                20                  25                  30

Trp Thr Gly Trp Arg Gly
        35
```

(2) INFORMATION FOR SEQ ID NO:6:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:6:

```
Cys Arg Tyr Val His Lys Val Ser Gly Thr Gly Pro Cys Ala Gly Asp
1               5                   10                  15

Phe Ala Phe His Lys Glu Gly Ala Phe Phe Leu Tyr Asp Arg Leu Ala
                20                  25                  30

Ser Thr Val Ile Tyr Arg Gly Thr Thr Phe
        35                  40
```

(2) INFORMATION FOR SEQ ID NO:7:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:7:

```
Ser Pro Gln Ser Leu Thr Thr Lys Pro Gly Pro Asp Asn Ser Thr His
1               5                   10                  15

Asn Thr Pro Val Tyr Lys Leu Asp Ile Ser Glu Ala Thr Gln Val Glu
                20                  25                  30

Gln
```

(2) INFORMATION FOR SEQ ID NO:8:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
            (A) ORGANISM: Ebola Virus
            (B) STRAIN: Zaire-Mayinga (xi) SEQUENCE DESCRIPTION: SEQ ID NO:8:

Ser Asp Thr Pro Ser Ala Thr Thr Ala Ala Gly Pro Pro Lys Ala Glu
1               5                   10                  15

Asn Thr Asn Thr Ser Lys Ser Thr Asp Phe Leu Asp Pro Ala Thr Thr
            20                  25                  30

Thr (2) INFORMATION FOR SEQ ID NO:9:

(i) SEQUENCE CHARACTERISTICS:
            (A) LENGTH: 51 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Ebola Virus
            (B) STRAIN: Zaire-Mayinga (xi) SEQUENCE DESCRIPTION: SEQ ID NO:9:

Asn Gln Asp Gly Leu Ile Cys Gly Leu Arg Gln Leu Ala Asn Glu Thr
1               5                   10                  15

Thr Gln Ala Leu Gln Leu Phe Leu Arg Ala Thr Thr Glu Leu Arg Thr
            20                  25                  30

Phe Ser Ile Leu Asn Arg Lys Ala Ile Asp Phe Leu Leu Gln Arg Trp
        35                  40                  45

Gly Gly Thr
    50

(2) INFORMATION FOR SEQ ID NO:10:

(i) SEQUENCE CHARACTERISTICS:
            (A) LENGTH: 51 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Marburg Virus
            (B) STRAIN: Popp (xi) SEQUENCE DESCRIPTION: SEQ ID NO:10:

Asn Gln Asn Asn Leu Val Cys Arg Leu Arg Arg Leu Ala Asn Gln Thr
1               5                   10                  15

Ala Lys Ser Leu Glu Leu Leu Leu Arg Val Thr Thr Glu Glu Arg Thr
            20                  25                  30

Phe Ser Leu Ile Asn Arg Arg Ala Ile Asp Phe Leu Leu Thr Arg Trp
        35                  40                  45

Gly Gly Thr
    50

(2) INFORMATION FOR SEQ ID NO:11:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: HIV-1

(xi) SEQUENCE DESCRIPTION: SEQ ID NO:11:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:12:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Rous Sarcoma Virus
        (B) STRAIN: Prague C (xi) SEQUENCE DESCRIPTION: SEQ ID NO:12:

Cys Glu Asp Ile Ala Gly Met Cys Cys Phe Asn Leu Ser Asp His Ser
1               5                   10                  15

Glu Ser Ile Gln Lys Lys Phe Gln Leu Met Lys Glu His Val Asn Lys
            20                  25                  30

Ile Gly Val Asp Ser Asp Pro Ile Gly Ser Trp Leu Arg Gly Leu Phe
        35                  40                  45

Gly Gly
    50

(2) INFORMATION FOR SEQ ID NO:13:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:13:

Cys His Ile Leu Gly Pro Asp Cys Cys Ile Glu Pro His Asp Trp Thr
1               5                   10                  15

```
Lys Asn Ile Thr Asp Lys Ile Asp Gln Ile Ile His Asp Phe Val Asp
            20                  25                  30

Lys Thr Leu Pro Asp Gln Gly Asp Asn Asp Asn Trp Trp Thr Gly Trp
        35                  40                  45

Arg Gln Trp
    50
```

(2) INFORMATION FOR SEQ ID NO:14:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Marburg Virus
        (B) STRAIN: Popp (xi) SEQUENCE DESCRIPTION: SEQ ID NO:14:

```
Cys Lys Val Leu Gly Pro Asp Cys Cys Ile Gly Ile Glu Asp Leu Ser
1               5                  10                  15

Lys Asn Ile Ser Glu Gln Ile Asp Gln Ile Lys Lys Asp Glu Gln Lys
            20                  25                  30

Glu Gly Thr Gly Trp Gly Leu Gly Gly Lys Trp Trp Thr Ser Asp Trp
        35                  40                  45

Gly Val
    50
```

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:15:

```
Phe Leu Leu Gln Arg Trp Gly
1               5
```

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Theoretical (xi) SEQUENCE DESCRIPTION: SEQ ID NO:16:

```
Phe Leu Leu Gln Arg Met Gly
1               5
```

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Theoretical (xi) SEQUENCE DESCRIPTION: SEQ ID NO:17:

```
Phe Leu Leu Gln Arg Trp Val
1               5
```

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Theoretical (xi) SEQUENCE DESCRIPTION: SEQ ID NO:18:

```
Phe Leu Leu Gln Arg Met Val
1               5
```

(2) INFORMATION FOR SEQ ID NO:19:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:19:

```
Ala Gly Val Ala Gly Leu Ile Thr Gly Gly Arg Arg Thr Arg Arg Glu
1               5                   10                  15

Ala Ile Val Asn Ala Gln Pro Lys
            20
```

(2) INFORMATION FOR SEQ ID NO:20:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
            (A) ORGANISM: Theoretical (xi) SEQUENCE DESCRIPTION: SEQ ID NO:20:

Trp Ile Pro Phe Phe Gly Pro
1               5

(2) INFORMATION FOR SEQ ID NO:21:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Ebola Virus
            (B) STRAIN: Zaire-Mayinga (xi) SEQUENCE DESCRIPTION: SEQ ID NO:21:

Trp Ile Pro Tyr Phe Gly Pro
1               5

(2) INFORMATION FOR SEQ ID NO:22:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Theoretical (xi) SEQUENCE DESCRIPTION: SEQ ID NO:22:

Pro Gly Phe Phe Pro Ile Trp
1               5

(2) INFORMATION FOR SEQ ID NO:23:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Theoretical (xi) SEQUENCE DESCRIPTION: SEQ ID NO:23:

Pro Gly Phe Tyr Pro Ile Trp
1               5

(2) INFORMATION FOR SEQ ID NO:24:

(i) SEQUENCE CHARACTERISTICS:
            (A) LENGTH: 46 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Ebola Virus
            (B) STRAIN: Zaire-Mayinga (xi) SEQUENCE DESCRIPTION: SEQ ID NO:24:

Cys Asn Pro Asn Leu His Tyr Trp Thr Thr Gln Asp Glu Gly Ala Ala
1               5                   10                  15

Ile Gly Leu Ala Trp Ile Pro Tyr Phe Gly Pro Ala Ala Glu Gly Ile
            20                  25                  30

Tyr Ile Glu Gly Leu Met His Asn Gln Asp Gly Leu Ile Cys
        35                  40                  45

(2) INFORMATION FOR SEQ ID NO:25:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Marburg Virus
            (B) STRAIN: Popp (xi) SEQUENCE DESCRIPTION: SEQ ID NO:25:

Asp Leu Ala Ala Gly Leu Ser Trp Ile Pro Phe Phe Gly Pro Gly Ile
1               5                   10                  15

Glu Gly Leu Tyr
        20

(2) INFORMATION FOR SEQ ID NO:26:

(i) SEQUENCE CHARACTERISTICS:
            (A) LENGTH: 46 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: Marburg Virus
            (B) STRAIN: Popp (xi) SEQUENCE DESCRIPTION: SEQ ID NO:26:

Cys Asp Ala Glu Leu Arg Ile Trp Ser Val Gln Glu Asp Asp Leu Ala
1               5                   10                  15

Ala Gly Leu Ser Trp Ile Pro Phe Phe Gly Pro Gly Ile Glu Gly Leu
            20                  25                  30

Tyr Thr Ala Val Leu Ile Lys Asn Gln Asn Asn Leu Val Cys
        35                  40                  45

(2) INFORMATION FOR SEQ ID NO:27:

(i) SEQUENCE CHARACTERISTICS:

(xi) SEQUENCE DESCRIPTION:SEQ ID NO:27:

This sequence is intentionally skipped.

(2) INFORMATION FOR SEQ ID NO:28:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:28:

Asn Gln Asp Gly Leu Ile Cys Gly Leu Arg Gln Leu Ala Asn Glu Thr
1            5                  10              15

Thr Gln Ala Leu Gln Leu Phe Leu Arg
          20                25

(2) INFORMATION FOR SEQ ID NO:29:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:29:

Ala Thr Thr Glu Leu Arg Thr Phe Ser Ile Leu Asn Arg Lys Ala Ile
1            5                  10              15

Asp Phe Leu Leu Gln Arg Trp Gly Gly Thr
          20                25

(2) INFORMATION FOR SEQ ID NO:30:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:30:

Leu Arg Gln Leu Ala Asn Glu Thr Thr Gln Ala Leu Gln Leu Phe Leu

-continued

```
1               5                   10                  15

Arg Ala Thr Thr Glu Leu Arg Thr Phe Ser Ile Leu Asn Arg Lys Ala
            20                  25                  30

Ile Asp Phe Leu Leu Gln Arg
        35

(2) INFORMATION FOR SEQ ID NO:31:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: peptide (v) FRAGMENT TYPE: internal (vi) ORIGINAL SOURCE:
          (A) ORGANISM: Ebola Virus
          (B) STRAIN: Zaire-Mayinga (xi) SEQUENCE DESCRIPTION: SEQ ID NO:31:

Gln Ala Leu Gln Leu Phe Leu Arg Ala Thr Thr Glu Leu Arg Thr Phe
1               5                   10                  15

Ser Ile Leu Asn Arg Lys
            20

(2) INFORMATION FOR SEQ ID NO:32:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (v) FRAGMENT TYPE: internal (vi) ORIGINAL SOURCE:
          (A) ORGANISM: Marburg Virus
          (B) STRAIN: Popp (xi) SEQUENCE DESCRIPTION: SEQ ID NO:32:

Cys Lys Val Leu Gly Pro Asp Cys Cys
1               5

(2) INFORMATION FOR SEQ ID NO:33:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (v) FRAGMENT TYPE: internal (vi) ORIGINAL SOURCE:
          (A) ORGANISM: Ebola Virus
          (B) STRAIN: Zaire-Mayinga (xi) SEQUENCE DESCRIPTION: SEQ ID NO:33:

Gln Arg Trp Gly Gly Thr Cys His Ile Leu Gly Pro Asp Cys Cys Ile
1               5                   10                  15

Glu Pro His Asp
            20
```

(2) INFORMATION FOR SEQ ID NO:34:

(i) SEQUENCE CHARACTERISTICS:

(xi) SEQUENCE DESCRIPTION:SEQ ID NO:34:

This sequence is intentionally skipped.

(2) INFORMATION FOR SEQ ID NO:35:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:35:

```
Ile Thr Asp Lys Ile Asp Gln His His Asp Phe Val Asp Lys Thr Leu
1               5                   10                  15
```

(2) INFORMATION FOR SEQ ID NO:36:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:36:

```
Gly Asp Asn Asp Asn Trp Trp Thr
1               5
```

(2) INFORMATION FOR SEQ ID NO:37:

(i) SEQUENCE CHARACTERISTICS:

(xi) SEQUENCE DESCRIPTION:SEQ ID NO:37:

This sequence is intentionally skipped.

(2) INFORMATION FOR SEQ ID NO:38:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Marburg Virus
        (B) STRAIN: Popp (xi) SEQUENCE DESCRIPTION: SEQ ID NO:38:

Glu Asp Leu Ser Lys Asn Ile Ser Glu Gln Ile Asp Gln Ile Lys Lys
1               5                   10                  15

Asp Glu Gln Lys Glu Gly Thr Gly Trp Gly Leu Gly Gly Lys Trp Trp
                20                  25                  30

Thr Ser Asp Trp Gly Val
            35

(2) INFORMATION FOR SEQ ID NO:39:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Marburg Virus
        (B) STRAIN: Popp (xi) SEQUENCE DESCRIPTION: SEQ ID NO:39:

Ile Ser Glu Gln Ile Asp Gln Ile Lys Lys Asp Glu Gln Lys Glu Gly
1               5                   10                  15

Thr (2) INFORMATION FOR SEQ ID NO:40:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:40:

His Lys Glu Gly Ala Phe Phe Leu Tyr Asp Arg
1               5                   10

(2) INFORMATION FOR SEQ ID NO:41:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:41:

Ser Leu Thr Thr Lys Pro Gly Pro Asp Asn Ser Thr His Asn Thr Pro
1               5                   10                  15

Val Tyr Lys (2) INFORMATION FOR SEQ ID NO:42:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:42:

Ser Ala Thr Thr Ala Ala Gly Pro Pro Lys Ala Glu Asn Thr Asn Thr
1               5                   10                  15

Ser Lys (2) INFORMATION FOR SEQ ID NO:43:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:43:

His Asp Trp Thr Lys Asn Ile Thr Asp Lys Ile Asp Gln Ile Ile His
1               5                   10                  15

Asp Phe Val Asp Lys Thr Leu Pro Asp Gln Gly Asp Asn Asp Asn
            20                  25                  30

(2) INFORMATION FOR SEQ ID NO:44:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Ebola Virus
        (B) STRAIN: Zaire-Mayinga (xi) SEQUENCE DESCRIPTION: SEQ ID NO:44:

His Asp Trp Thr Lys Asn Ile Thr Asp Lys Ile Asp Gln Ile Ile His
1               5                   10                  15

Asp Phe Val Asp Lys Thr Leu
            20

(2) INFORMATION FOR SEQ ID NO:45:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (v) FRAGMENT TYPE: internal (vi) ORIGINAL SOURCE:
    (A) ORGANISM: Ebola Virus
    (B) STRAIN: Zaire-Mayinga (xi) SEQUENCE DESCRIPTION: SEQ ID NO:45:

```
Asp Lys Ile Asp Gln Ile Ile His Asp Phe Val Asp Lys Thr Leu
1               5                   10                  15
```

(2) INFORMATION FOR SEQ ID NO:46:

(i) SEQUENCE CHARACTERISTICS:
    (A) LENGTH: 23 amino acids
    (B) TYPE: amino acid
    (C) STRANDEDNESS: single
    (D) TOPOLOGY: linear (ii) MOLECULE TYPE: peptide (v) FRAGMENT TYPE: internal (vi) ORIGINAL SOURCE:
    (A) ORGANISM: Ebola Virus
    (B) STRAIN: Zaire-Mayinga (xi) SEQUENCE DESCRIPTION: SEQ ID NO:46:

```
Asp Lys Ile Asp Gln Ile Ile His Asp Phe Val Asp Lys Thr Leu Pro
1               5                   10                  15

Asp Gln Gly Asp Asn Asp Asn
                20
```

(2) INFORMATION FOR SEQ ID NO:47:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (v) FRAGMENT TYPE: internal (vi) ORIGINAL SOURCE:
    (A) ORGANISM: Marburg Virus
    (B) STRAIN: Popp (xi) SEQUENCE DESCRIPTION: SEQ ID NO:47:

```
Asn Phe Ser Thr Leu Ser Ala Pro Leu Gln Thr Thr Asn Asp Asn Thr
1               5                   10                  15

Gln Ser
```

(2) INFORMATION FOR SEQ ID NO:48:

(i) SEQUENCE CHARACTERISTICS:
    (A) LENGTH: 23 amino acids
    (B) TYPE: amino acid
    (C) STRANDEDNESS: single
    (D) TOPOLOGY: linear (ii) MOLECULE TYPE: peptide (v) FRAGMENT TYPE: internal (vi) ORIGINAL SOURCE:
             (A) ORGANISM: Marburg Virus
             (B) STRAIN: Popp (xi) SEQUENCE DESCRIPTION: SEQ ID NO:48:

Ser Lys Lys Gly Pro Ala Thr Thr Ala Pro Asn Thr Thr Asn Glu His
 1               5                  10                  15

Phe Thr Ser Pro Pro Thr Pro
             20

(2) INFORMATION FOR SEQ ID NO:49:

(i) SEQUENCE CHARACTERISTICS:
             (A) LENGTH: 154 amino acids
             (B) TYPE: amino acid
             (C) STRANDEDNESS: single
             (D) TOPOLOGY: linear (ii) MOLECULE TYPE: protein (v) FRAGMENT TYPE: internal (vi) ORIGINAL SOURCE:
             (A) ORGANISM: Ebola Virus
             (B) STRAIN: Zaire-Mayinga (xi) SEQUENCE DESCRIPTION: SEQ ID NO:49:

Arg Arg Thr Arg Arg Glu Ala Ile Val Asn Ala Gln Pro Lys Cys Asn
 1               5                  10                  15

Pro Asn Leu His Tyr Trp Thr Thr Gln Asp Glu Gly Ala Ala Ile Gly
             20                  25                  30

Leu Ala Trp Ile Pro Tyr Phe Gly Pro Ala Ala Glu Gly Ile Tyr Ile
         35                  40                  45

Glu Gly Leu Met His Asn Gln Asp Gly Leu Ile Cys Gly Leu Arg Gln
     50                  55                  60

Leu Ala Asn Glu Thr Thr Gln Ala Leu Gln Leu Phe Leu Arg Ala Thr
65                  70                  75                  80

Thr Glu Leu Arg Thr Phe Ser Ile Leu Asn Arg Lys Ala Ile Asp Phe
                 85                  90                  95

Leu Leu Gln Arg Trp Gly Gly Thr Cys His Ile Leu Gly Pro Asp Cys
            100                 105                 110

Cys Ile Glu Pro His Asp Trp Thr Lys Asn Ile Thr Asp Lys Ile Asp
        115                 120                 125

Gln Ile Ile His Asp Phe Val Asp Lys Thr Leu Pro Asp Gln Gly Asp
    130                 135                 140

Asn Asp Asn Trp Trp Thr Gly Trp Arg Gln
145                 150

(2) INFORMATION FOR SEQ ID NO:50:

(i) SEQUENCE CHARACTERISTICS:
             (A) LENGTH: 153 amino acids
             (B) TYPE: amino acid
             (C) STRANDEDNESS: single
             (D) TOPOLOGY: linear (ii) MOLECULE TYPE: protein (v) FRAGMENT TYPE: internal (vi) ORIGINAL SOURCE:
             (A) ORGANISM: Marburg Virus (B) STRAIN: Popp (xi) SEQUENCE DESCRIPTION: SEQ ID NO:50:

```
Arg Arg Lys Arg Ser Val Ser His Leu Asp Asp Thr Cys Ser Asp Glu
1               5                   10                  15

Val Gln Leu Trp Gly Pro Thr Ala Arg Ile Phe Ala Ser Ile Leu Ala
            20                  25              30

Pro Gly Val Ala Ala Ala Gln Ala Leu Arg Glu Ile Glu Arg Leu Ala
        35              40              45

Cys Trp Ser Val Lys Gln Ala Asn Leu Thr Thr Ser Leu Leu Gly Asp
    50              55              60

Leu Leu Asp Asp Val Thr Ser Ile Arg His Ala Val Leu Gln Asn Arg
65              70              75                      80

Ala Ala Ile Asp Phe Leu Leu Ala His Gly His Gly Cys Glu Asp
                85              90              95

Val Ala Gly Met Cys Cys Phe Asn Leu Ser Asp His Ser Glu Ser Ile
            100             105                 110

Gln Lys Lys Phe Gln Leu Met Lys Lys His Val Asn Lys Ile Gly Val
            115             120             125

Asp Ser Asp Pro Ile Gly Ser Trp Leu Arg Gly Leu Phe Gly Gly Ile
        130             135                 140

Gly Glu Trp Ala Val His Leu Leu Lys
145             150
```